US00PP19090P2

(12) United States Plant Patent
Buffinga

(10) Patent No.: US PP19,090 P2
(45) Date of Patent: Aug. 12, 2008

(54) ***HIBISCUS* PLANT NAMED 'HJ-117'**

(50) Latin Name: *Hibiscus rosa-sinensis*
Varietal Denomination: HJ-117

(76) Inventor: Henry Albert Buffinga, RR 2, Seaforth, Ontario (CA), N0M 1L0

( * ) Notice: Subject to any disclaimer, the term of this patent is extended or adjusted under 35 U.S.C. 154(b) by 0 days.

(21) Appl. No.: 11/799,075

(22) Filed: Apr. 30, 2007

(51) Int. Cl.
*A01H 5/00* (2006.01)

(52) U.S. Cl. ..... Plt./257

(58) Field of Classification Search ..... Plt./257
See application file for complete search history.

*Primary Examiner*—Annette H Para
(74) *Attorney, Agent, or Firm*—C. A. Whealy

(57) ABSTRACT

A new and distinct cultivar of *Hibiscus* plant named 'HJ-117', characterized by its upright and somewhat outwardly spreading plant habit; freely branching habit when pinched; relatively large leaves; large yellow-colored flowers with white-colored centers; and long flower longevity.

2 Drawing Sheets

Botanical designation: *Hibiscus rosa-sinensis.*
Cultivar denomination: 'HJ-117'.

BACKGROUND OF THE INVENTION

The present invention relates to a new and distinct cultivar of *Hibiscus,* botanically known as *Hibiscus rosa-sinensis,* and hereinafter referred to by the name 'HJ-117'.

The new *Hibiscus* is a product of a planned breeding program conducted by the Inventor in Seaforth, Ontario, Canada. The objective of the breeding program is to create new *Hibiscus* cultivars that flower early and have long flower longevity.

The new *Hibiscus* originated from a cross-pollination made by the Inventor in Seaforth, Ontario, Canada in November, 2002, of the *Hibiscus rosa-sinensis* cultivar Byron Metts, not patented, as the female, or seed, parent with a proprietary *Hibiscus rosa-sinensis* selection, designated as code number HJ-136, not patented, as the male, or pollen, parent. The cultivar HJ-117 was discovered and selected by the Inventor as a flowering plant within the progeny of the stated cross-pollination in a controlled environment in Seaforth, Ontario, Canada in October, 2003.

Asexual reproduction of the new *Hibiscus* by vegetative terminal cuttings in a controlled environment in Seaforth, Ontario, Canada since January, 2004, has shown that the unique features of this new *Hibiscus* are stable and reproduced true to type in successive generations.

SUMMARY OF THE INVENTION

The cultivar HJ-117 has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'HJ-117'. These characteristics in combination distinguish 'HJ-117' as a new and distinct cultivar of *Hibiscus:*

1. Upright and somewhat outwardly spreading plant habit.
2. Freely branching habit when pinched.
3. Relatively large leaves.

4. Large yellow-colored flowers with white-colored centers.
5. Long flower longevity.

Plants of the new *Hibiscus* can be compared to plants of the female parent, the cultivar Byron Metts. Plants of the new *Hibiscus* differ from plants of the cultivar Byron Metts in the following characteristics:

1. Plants of the new *Hibiscus* have smaller and lighter green-colored leaves than plants of the cultivar Byron Metts.
2. Plants of the new *Hibiscus* have smaller flowers than plants of the cultivar Byron Metts.
3. Plants of the new *Hibiscus* and the cultivar Byron Metts differ in flower coloration as plants of the cultivar Byron Metts have solid white-colored flowers.

Plants of the new *Hibiscus* can be compared to plants of the male parent, the proprietary *Hibiscus* selection identified as code number HJ-136. Plants of the new *Hibiscus* differ from plants of the male parent selection in the following characteristics:

1. Plants of the new *Hibiscus* have smaller leaves than plants of the male parent selection.
2. Plants of the new *Hibiscus* and the male parent selection differ in flower coloration as plants of the male parent selection have white and purple-colored flowers.
3. Plants of the new *Hibiscus* have longer lasting flowers than plants of the male parent selection.
4. Plants of the new *Hibiscus* root more easily than plants of the male parent selection.

Plants of the new *Hibiscus* can be compared to plants of the *Hibiscus rosa-sinensis* cultivar Coconut Cream, not patented. In side-by-side comparisons conducted in Seaforth, Ontario, Canada, plants of the new *Hibiscus* differed from plants of the cultivar Coconut Cream in the following characteristics:

1. Plants of the new *Hibiscus* had darker green-colored leaves than plants of the cultivar Coconut Cream.

2. Plants of the new *Hibiscus* were more freely branching than plants of the cultivar Coconut Cream.
3. Plants of the new *Hibiscus* had longer lasting flowers than plants of the cultivar Coconut Cream.
4. Plants of the new *Hibiscus* rooted more easily than plants of the cultivar Coconut Cream.

Plants of the new *Hibiscus* can be compared to plants of the *Hibiscus rosa-sinensis* cultivar HJ-116, disclosed in U.S. Plant Pat. No. 18,586. In side-by-side comparisons conducted in Seaforth, Ontario, Canada, plants of the new *Hibiscus* differed from plants of the cultivar HJ-116 in the following characteristics:

1. Plants of the new *Hibiscus* had longer lateral branches and internodes than plants of the cultivar HJ-116.
2. Plants of the new *Hibiscus* had smaller flowers than plants of the cultivar HJ-116.
3. Plants of the new *Hibiscus* and the cultivar HJ-116 differed in flower color.
4. Plants of the new *Hibiscus* had longer peduncles than plants of the cultivar HJ-116.

BRIEF DESCRIPTION OF THE PHOTOGRAPHS

The accompanying colored photographs illustrate the overall appearance of the new *Hibiscus,* showing the colors as true as it is reasonably possible to obtain in colored reproductions of this type. Colors in the photographs may differ slightly from the color values cited in the detailed botanical description which accurately describe the colors of the new *Hibiscus.*

The photograph on the first sheet comprises a side perspective view of typical flowering plants of 'HJ-117' grown in a container.

The photograph on the second sheet is a close-up view of a typical flower of 'HJ-117'.

DETAILED BOTANICAL DESCRIPTION

The aforementioned photographs and following observations, measurements and values describe plants grown in Seaforth, Ontario, Canada in containers during the winter and spring in polyethylene-covered greenhouses under conditions which closely approximate commercial production. During the production of the plants, day temperatures ranged from about 20° C. to about 28° C. and night temperatures ranged from about 18° C. to about 20° C. Plants were about five months old when the photograph and the description were taken. In the description, color references are made to The Royal Horticultural Society Colour Chart, 2001 Edition, except where general terms of ordinary dictionary significance are used.

Botanical classification: *Hibiscus rosa-sinensis* cultivar HJ-117.

Parentage:

*Female, or seed, parent.*—*Hibiscus rosa-sinensis* cultivar Byron Metts, not patented.

*Male or pollen parent.*—Proprietary selection of *Hibiscus rosa-sinensis* designated as code number HJ-136, not patented.

Propagation:

*Type.*—By vegetative terminal cuttings.

*Time to initiate roots.*—About 30 days at 28° C.

*Time to develop roots.*—About 45 days at 28° C.

*Root description.*—Thick, fleshly; white in color.

*Rooting habit.*—Moderately dense.

Plant description:

*Plant form and growth habit.*—Upright and somewhat outwardly spreading plant habit. Moderately vigorous growth habit.

*Branching habit.*—Freely branching, usually about three lateral branches develop after pinching (removal of terminal apex).

*Plant height.*—About 43.2 cm.

*Plant diameter* (*area of spread*).—About 35 cm to 40 cm.

Lateral branch description:

*Length.*—About 21.3 cm.

*Diameter.*—About 4 mm to 5 mm.

*Internode length.*—About 4.4 cm.

*Texture, immature.*—Sparsely pubescent.

*Texture, mature.*—Woody, rough.

*Color, immature.*—144A.

*Color, mature.*—199D.

Foliage description:

*Arrangement.*—Alternate, single.

*Length.*—About 10.7 cm.

*Width.*—About 6.6 cm.

*Shape.*—Ovate.

*Apex.*—Narrowly acute.

*Base.*—Crenate to obtuse.

*Margin.*—Crenate.

*Texture, upper and lower surfaces.*—Sparsely pubescent; rugose.

*Venation pattern.*—Palmate.

*Color.*—Developing foliage, upper surface: 147A. Developing foliage, lower surface: 147B. Mature foliage, upper surface: Darker than 139A; venation, similar to lamina. Mature foliage, lower surface: Close to 137B; venation, similar to lamina.

*Petiole.*—Length: About 5.1 cm. Diameter: About 3 mm. Texture, upper and lower surfaces: Smooth, glabrous. Color, upper surface: 147A. Color, lower surface: 137B.

Flower description:

*Flower appearance/arrangement.*—Rounded flowers arranged singly at terminal leaf axils. Uniform and freely flowering habit with usually about three or four flower buds and/or open flowers per terminal apex. Flowers face upright to outwardly.

*Flower longevity.*—Flowers are long lasting, lasting for about three to seven days. Flowers not persistent.

*Natural flowering season.*—Usually spring and summer or during periods of warm weather.

*Flower diameter.*—About 15.1 cm.

*Flower length* (*height*).—About 8.5 cm.

*Flower bud.*—Length: About 6.6 cm. Diameter: About 2 cm. Shape: Elliptic. Color: 154C.

*Petals.*—Arrangement: Corolla consists of five imbricate petals. Length: About 9.9 cm. Width: About 7.8 cm. Shape: Spatulate. Apex: Rounded. Base: Attenuate. Margin: Entire; weakly undulate. Texture, upper and lower surfaces: Smooth, glabrous. Color: When opening and fully opened, upper surface: 10A; towards the base, 155C; occasionally, petal base blushed with 56C. When opening and fully opened, lower surface: 10B.

*Sepals.*—Appearance: Five sepals fused into tubular calyx. Length: About 2.7 cm. Width: About 1 cm. Shape: Rhombic. Apex: Cuspidate. Margin: Entire. Texture, upper and lower surfaces: Smooth, glabrous. Color, upper and lower surfaces: 144B.

*Bracts.*—Appearance: About seven fused at base. Length: About 1.7 cm. Width: About 3 mm to 4 mm. Shape: Linear. Apex: Acuminate. Margin: Entire. Texture, upper and lower surfaces: Smooth, glabrous. Color, upper and lower surfaces: Close to 147A.

*Peduncles.*—Length: About 12 cm. Diameter: About 2 mm to 3 mm. Strength: Strong, flexible. Texture: Smooth, glabrous. Color: 144A.

*Reproductive organs.*—Androecium: Stamen number: Numerous, about 65. Filament length: About 2 mm. Filament color: Close to 155A. Anther shape: Globular. Anther length: About 1 mm. Anther color: Close to 4D. Amount of pollen: Abundant. Pollen color: Close to 17A. Gynoecium: Pistil length: About 6.5 cm. Style length: About 6 cm. Style texture: Smooth, waxy. Style color: 4D. Stigma appearance: Five, spherical. Stigma diameter: About 2 mm. Stigma color: 13A. Ovary color: Close to 154D.

*Seed/fruit.*—Seed and fruit production has not been observed.

Temperature tolerance: Plants of the new *Hibiscus* have been observed to tolerate temperatures from about 10° C. to about 35° C.

Pathogen/pest resistance: Plants of the new *Hibiscus* have not been shown to be resistant to pathogens and pests common to *Hibiscus*.

It is claimed:

1. A new and distinct *Hibiscus* plant named 'HJ-117' as illustrated and described.

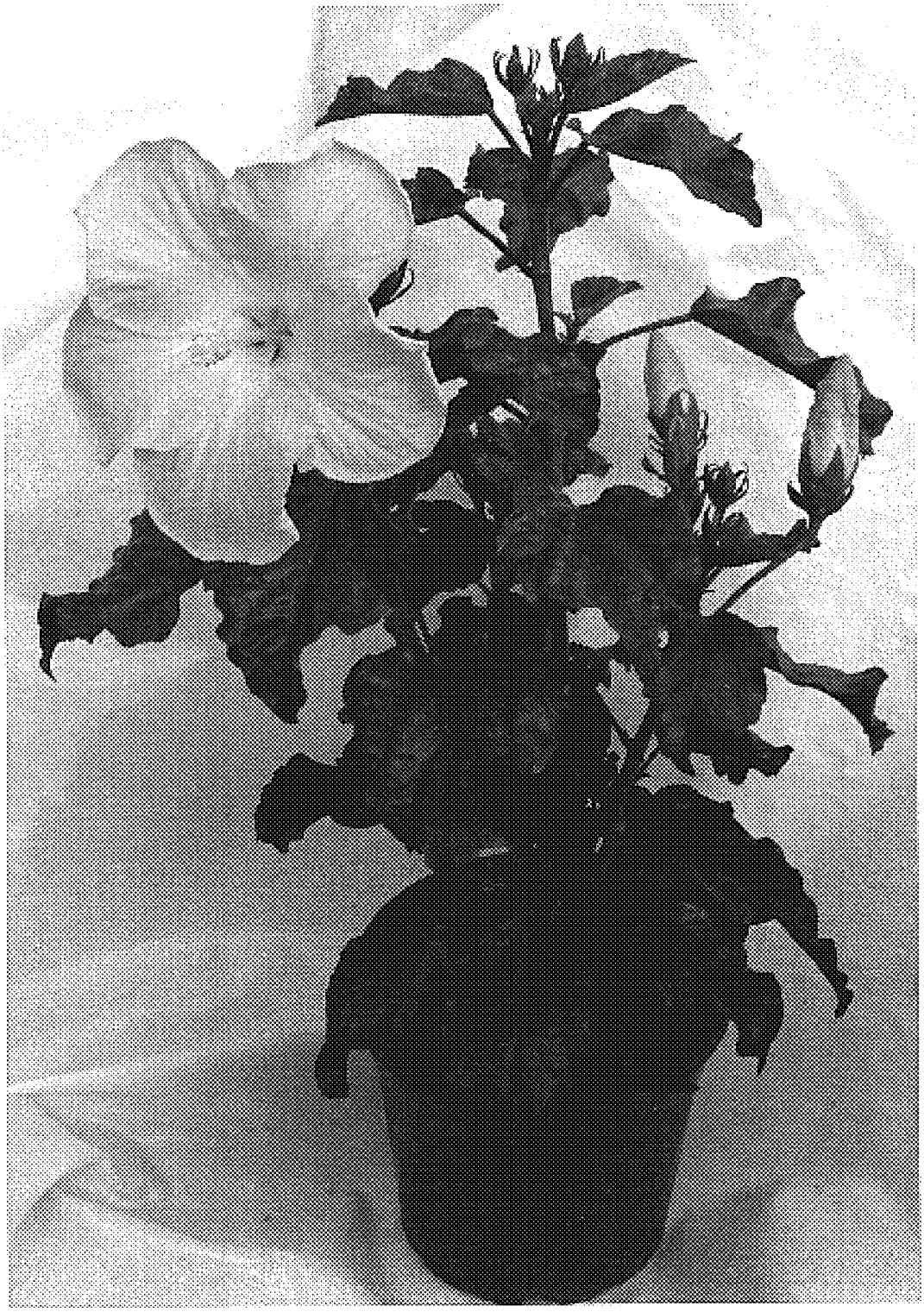

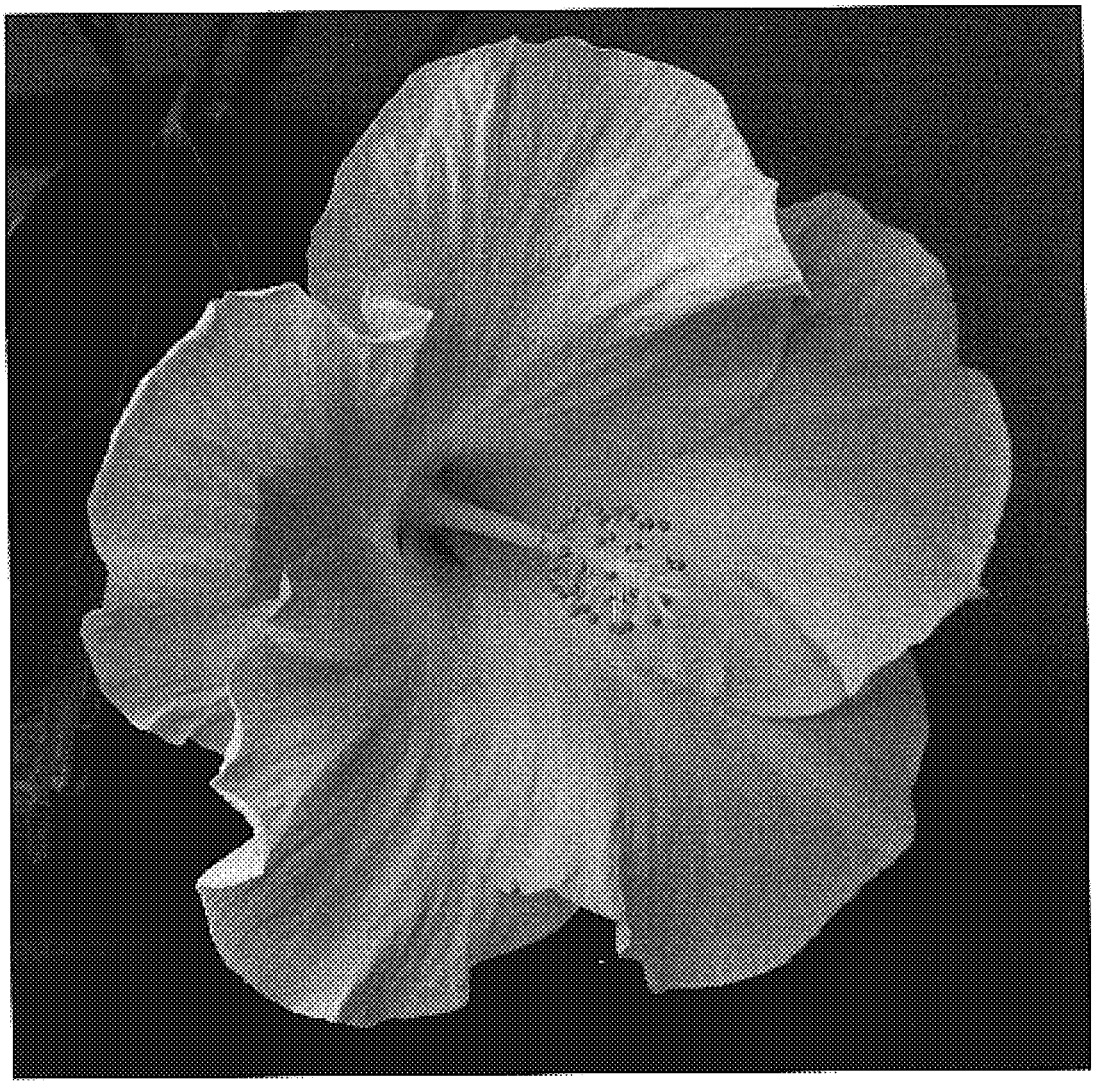

* * * * *